(12) United States Patent
Fiering et al.

(10) Patent No.: US 12,265,077 B2
(45) Date of Patent: Apr. 1, 2025

(54) ACOUSTIC SEPARATION OF PARTICLES FOR BIOPROCESSING

(71) Applicant: THE CHARLES STARK DRAPER LABORATORY, INC., Cambridge, MA (US)

(72) Inventors: Jason O. Fiering, Boston, MA (US); Kenneth T. Kotz, Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 494 days.

(21) Appl. No.: 16/661,845

(22) Filed: Oct. 23, 2019

(65) Prior Publication Data

US 2020/0057045 A1 Feb. 20, 2020

Related U.S. Application Data

(62) Division of application No. 15/965,368, filed on Apr. 27, 2018, now Pat. No. 10,914,723.
(Continued)

(51) Int. Cl.
*G01N 33/49* (2006.01)
*A61M 1/36* (2006.01)
(Continued)

(52) U.S. Cl.
CPC ......... *G01N 33/491* (2013.01); *A61M 1/3678* (2014.02); *A61M 1/3693* (2013.01);
(Continued)

(58) Field of Classification Search
CPC .............. A61M 1/3616; A61M 1/3678; A61M 1/3693; B01D 21/283; B01D 2221/10;
(Continued)

(56) References Cited

U.S. PATENT DOCUMENTS 8,134,705 B2 * 3/2012 Kaduchak ............ G01N 29/222
356/337
9,663,756 B1 5/2017 Lipkens et al.
(Continued)

FOREIGN PATENT DOCUMENTS

JP 2007/504446 A 3/2007
JP 2012513287 A 6/2012
(Continued)

OTHER PUBLICATIONS

Grenvall et al., "Concurrent Isolation of Lymphocytes and Granulocytes Using Prefocused Free Flow Acoustophoresis", Anal. Chem., vol. 87, No. 11, 2015, pp. 5596-5604.
(Continued)

*Primary Examiner* — Dirk R Bass
(74) *Attorney, Agent, or Firm* — Brooks Kushman, P.C.

(57) ABSTRACT

A method for separating particles in a biofluid includes pretreating the biofluid by introducing an additive, flowing the pretreated biofluid through a microfluidic separation channel, and applying acoustic energy to the microfluidic separation channel. A system for microfluidic separation, capable of separating target particles from non-target particles in a biofluid includes at least one microfluidic separation channel, a source of biofluid, a source of additive, and at least one acoustic transducer coupled to the microfluidic separation channel. A kit for microfluidic particle separation includes a microfluidic separation channel connected to an acoustic transducer, a source of an additive, and instructions for use.

29 Claims, 5 Drawing Sheets

Related U.S. Application Data

(60) Provisional application No. 62/492,044, filed on Apr. 28, 2017.

(51) Int. Cl.
| | |
|---|---|
| *B01D 21/28* | (2006.01) |
| *B01L 3/00* | (2006.01) |
| *B03B 1/04* | (2006.01) |
| *G01N 15/02* | (2024.01) |
| *G01N 15/06* | (2024.01) |
| *G01N 15/01* | (2024.01) |
| *G01N 15/10* | (2006.01) |

(52) U.S. Cl.
CPC ...... *B01D 21/283* (2013.01); *B01L 3/502753* (2013.01); *B03B 1/04* (2013.01); *G01N 15/02* (2013.01); *G01N 15/06* (2013.01); *B01D 2221/10* (2013.01); *B01L 3/502761* (2013.01); *B01L 2200/0652* (2013.01); *B01L 2400/0436* (2013.01); *G01N 15/01* (2024.01); *G01N 2015/0288* (2013.01); *G01N 2015/0681* (2013.01); *G01N 2015/0687* (2013.01); *G01N 2015/1006* (2013.01); *G01N 2015/1028* (2024.01)

(58) Field of Classification Search
CPC ..... B01L 2200/0652; B01L 2400/0436; B01L 3/502753; B01L 3/502761; B03B 1/04; G01N 15/02; G01N 15/06; G01N 2015/0065; G01N 2015/0288; G01N 2015/0681; G01N 2015/0687; G01N 2015/1006; G01N 2015/1081; G01N 33/491

See application file for complete search history.

(56) References Cited

U.S. PATENT DOCUMENTS

| | | |
|---|---|---|
| 10,370,635 B2 | 8/2019 | Lipkens et al. |
| 10,640,760 B2 | 5/2020 | Lipkens et al. |
| 10,745,741 B2 | 8/2020 | Utharala et al. |
| 10,962,525 B2 | 3/2021 | Rendu et al. |
| 2004/0069717 A1 | 4/2004 | Laurell et al. |
| 2007/0269887 A1 | 11/2007 | Coelho et al. |
| 2009/0029870 A1 | 1/2009 | Ward et al. |
| 2011/0201099 A1 | 8/2011 | Anderson et al. |
| 2012/0214224 A1 | 8/2012 | Chan |
| 2013/0224777 A1 | 8/2013 | Patzke |
| 2013/0337529 A1 | 12/2013 | Choo |
| 2014/0069865 A1 | 3/2014 | Yvert et al. |
| 2014/0230912 A1 | 8/2014 | Aider et al. |
| 2014/0273192 A1 | 9/2014 | Sharpe et al. |
| 2015/0017678 A1 | 1/2015 | Matula et al. |
| 2015/0253226 A1* | 9/2015 | Augustsson ..... G01N 33/56972 435/7.25 |
| 2016/0030660 A1 | 2/2016 | Sun et al. |
| 2016/0103066 A1 | 4/2016 | Schasfoort |
| 2017/0042770 A1 | 2/2017 | Warner et al. |
| 2017/0260493 A1* | 9/2017 | Lipkens ................ C12M 47/02 |
| 2018/0362918 A1 | 12/2018 | Lipkens et al. |
| 2020/0316603 A1 | 10/2020 | Kashanin et al. |

FOREIGN PATENT DOCUMENTS

| | | | |
|---|---|---|---|
| WO | 2007128795 A2 | 11/2007 | |
| WO | 2014046605 A1 | 3/2014 | |
| WO | 2014/138739 A1 | 9/2014 | |
| WO | 2016062975 A1 | 4/2016 | |
| WO | WO-2017035262 A1 * | 3/2017 | ............. A61K 35/12 |
| WO | 2018065626 A1 | 4/2018 | |

OTHER PUBLICATIONS

Lenshof et al., "Efficient purification of CD4+ lymphocytes from peripheral blood progenitor cell products using affinity bead acoustophoresis", Cytometry Part A, vol. 85, No. 11, 2014, pp. 933-941.

Petersson et al., "Free Flow Acoustophoresis: Microfluidic-Based Mode of Particle and Cell Separation", Anal. Chem. vol. 79, No. 14, 2007, pp. 5117-5123.

International Search Report and Written Opinion in application No. PCT/US2017/030232 dated Sep. 15, 2017.

Dykes et al. "Efficient Removal of Platelets from Peripheral Blood Progenitor Cell Products Using a Novel Micro-Chip Based Acoustophoretic Platform", PLOS One, (2011) vol. 6, No. 3, pp. E23074-1-10.

Ye et al. "Separation of *Escherichia coli* Bacteria from Peripheral Blood Mononuclear Cells Using Standing Surface Acoutsito Waves", Analytical Chemistry (2013) vol. 85, No. 19, pp. 9126-9134.

Invitation to Pay Additional Fees in application No. PCT/US2018/029934 dated Aug. 7, 2018.

Cushing et al. "Elastomeric Negative Acoustic Contrast Particles for Affinity Capture Assays", Analytical Chemistry (2013) vol. 85, pp. 2208-2215.

International Search Report and Written Opinion in application No. PCT/US2018/029934 dated Oct. 8, 2018.

International Preliminary Report on Patentability on PCT Appl. Ser. No. PCT/US2018/029934 dated Nov. 7, 2019 (18 pages).

US Non-Final Office Action on U.S. Appl. No. 15/965,368 dated Jan. 22, 2020 (10 pages).

US Non-Final Office Action on U.S. Appl. No. 17/171,651 dated Sep. 23, 2022 (11 pages).

US Notice of Allowance on U.S. Appl. No. 15/965,368 dated Oct. 30, 2020 (9 pages).

\* cited by examiner

ACOUSTIC SEPARATION OF PARTICLES FOR BIOPROCESSING

CROSS-REFERENCE TO RELATED APPLICATIONS

This application claims priority under 35 U.S.C. § 121 as a division of U.S. patent application Ser. No. 15/965,368, titled "ACOUSTIC SEPARATION OF PARTICLES FOR BIOPROCESSING," filed Apr. 27, 2018, which claims priority under 35 U.S.C. § 119 to U.S. Provisional Patent Application No. 62/492,044 titled "ACOUSTIC SEPARATION OF PARTICLES FOR BIOPROCESSING" filed on Apr. 28, 2017, each of which is hereby incorporated by reference in its entirety for all purposes.

FIELD OF TECHNOLOGY

Aspects and embodiments disclosed herein relate to systems and methods for the separation of particles in a biofluid. In particular, aspects and embodiments disclosed herein relate to systems and methods for the separation of target particles in a biofluid from non-target particles in the biofluid.

SUMMARY

In accordance with an aspect, there is provided a method of separating target particles from non-target particles in a biofluid. Specifically, there is provided a method for separating target particles that were introduced into the biofluid to provide a therapeutic treatment to at least one component of the biofluid. The method may comprise pretreating the biofluid, flowing the pretreated biofluid into an inlet of a microfluidic separation channel, and applying acoustic energy to the microfluidic separation channel to accumulate target particles within a primary stream along the separation channel and accumulate non-target particles within a secondary stream along the separation channel. In some embodiments, pretreating the biofluid comprises introducing an additive into the biofluid to alter at least one of size of the target particles, size of the non-target particles, compressibility of the biofluid, compressibility of the target particles, compressibility of the non-target particles, aggregation potential of the target particles, and aggregation potential of the non-target particles. The method may further comprise introducing an additive to alter at least one of density of the biofluid, density of the target particles, and density of the non-target particles. In some embodiments, the acoustic energy may be applied transverse to a direction of the fluid flow through the separation channel.

In some embodiments, the method further comprises selecting the biofluid from blood buffy coat, leukapheresis product, peripheral blood, whole blood, lymph fluid, synovial fluid, spinal fluid, bone marrow, ascities fluid, and combinations or subcomponents thereof.

According to some embodiments, the method further comprises selecting the target particles to be synthetic particles selected from the group consisting of carrier particles, capture particles, enrichment particles, delivery particles, subclasses thereof, and combinations thereof. In some embodiments the target particles were introduced into the biofluid to provide a therapeutic treatment to at least one component of the biofluid. For instance, the therapeutic treatment provided by the target particle prior to pretreating the biofluid may be selected from the group consisting of delivering a therapeutic moiety, capturing a therapeutic moiety, capturing a toxin, capturing a cell type, capturing a synthetic particle, culturing a cell type, and combinations thereof.

In accordance with one embodiment, there is provided a method of separating synthetic particles from non-target particles. According to certain embodiments, there is provided a method of separating carrier particles from non-target particles. According to some embodiments the method comprises selecting the target particles to be cell culture carrier particles.

The biofluid may be collected from a donor subject. The secondary stream may be post-treated and delivered to a recipient subject. In some embodiments, the recipient subject is the same as the donor subject. The method may be performed in line such that the biofluid is collected from a subject, target particles are separated from non-target particles in the biofluid by a method as described herein, a fluid depleted of target particles may be post-treated, and the post-treated fluid may be delivered back to the subject. In some embodiments, the donor subject and the recipient subject are not the same subject. The fluid depleted of target particles may be collected and stored for delivery to the recipient subject at a later time.

The method may further comprise flowing the fluid comprising the target particles through microfluidic separation channels arranged in series and applying acoustic energy to each separation channel. In some embodiments, the biofluid comprising target particles may be flowed through a first microfluidic separation channel to produce a primary stream enriched in target particles and a secondary stream depleted of target particles. The secondary stream may then be flowed through a second microfluidic separation channel to produce a second or subsequent secondary stream having a higher purity of non-target particles.

In some embodiments, the biofluid comprises non-target particles bound to the target particles. The method may further comprise treating the biofluid to unbind the non-target particles from the target particles prior to pretreating the biofluid for separation.

According to certain embodiments, the method further comprises flowing a second fluid adjacent to the biofluid into an inlet of the microfluidic separation channel. The biofluid and the second fluid may flow through the separation channel in substantially parallel and substantially laminar form.

In some embodiments the non-target particles comprise at least one of live cells, frozen cells, preserved cells, or cells grown in a cell culture. In some embodiments, the microfluidic separation channel is formed of a thermoplastic material. The microfluidic separation channel may be disposable.

In accordance with another aspect, there is provided a system for microfluidic particle separation. The system may be configured to separate target particles from non-target particles in a biofluid. Specifically, the system may be configured to separate target particles introduced into a biofluid to provide a therapeutic treatment to at least one component of the biofluid. In some embodiments, the system comprises at least one microfluidic separation channel comprising at least one inlet, a first outlet, and a second outlet, a source of biofluid in fluid communication with the microfluidic separation channel, a source of additive in fluid communication with the source of the biofluid, configured to introduce at least one additive into the biofluid, and at least one acoustic transducer coupled to a wall of the microfluidic separation channel. The acoustic transducer may be positioned to apply a standing acoustic wave transverse to the microfluidic separation channel. Systems that comprise more than one microfluidic separation channel may comprise one acoustic transducer coupled to each microfluidic separation channel or one or more acoustic transducers coupled to a collection of microfluidic separation channels.

In some embodiments, the system comprises at least two microfluidic separation channels. The at least two microfluidic separation channels may be arranged in a parallel arrangement. The system may further comprise a manifold configured to distribute biofluid to the at least two microfluidic separation channels. In some embodiments, the manifold is configured to distribute the biofluid in response to the input biofluid load on the system. The system may further comprise a sensor configured to measure an input biofluid load on the system. The sensor may be in electrical communication with the manifold, such that the manifold may distribute the biofluid to the microfluidic separation channels in response to the measurement of the input biofluid load.

In some embodiments, the system further comprises at least one sensor configured to measure at least one of density of the biofluid, hematocrit (HCT %) of the biofluid, concentration of target particles, or concentration of non-target particles in the biofluid. The system may further comprise a control module in electrical communication with the biofluid sensor. The control module may be in electrical communication with the source of additive, and configured to introduce a predetermined volume of the additive into the biofluid in response to the measurement of density of the biofluid or concentration of target particles or non-target particles. In certain embodiments the predetermined volume of the additive is determined to alter or regulate the biofluid to have a desired density, HCT %, or concentration of target particles or non-target particles.

According to certain embodiments, the system further comprises at least one sensor configured to measure a parameter of an output suspension. The sensors may measure HCT %, concentration of target particles, or concentration of non-target particles in the primary or secondary stream. The system may further comprise a control module in electrical communication with the output suspension sensor. The control module may be in electrical communication with the acoustic transducer, and configured to alter or regulate at least one input parameter of the acoustic transducer. For instance, the control module may alter or regulate the power, voltage, or frequency delivered to the acoustic transducer in response to a measurement of a parameter of the output suspension. For instance, the control module may be configured to act in response to a measurement of HCT %, concentration of target particles, or concentration of non-target particles in the output suspension. The control module in communication with the output suspension sensor may be the same or different from the control module in communication with the biofluid sensor.

The system may further comprise a source of a second fluid in fluid communication with the at least one inlet of the at least one microfluidic separation channel. The source of the second fluid may be configured to introduce the second fluid into the biofluid. In some embodiments, the biofluid and the second fluid flow in substantially parallel, substantially laminar flow.

In some embodiments, the system may further comprise a first and second collection channel in fluid communication with the at least one outlet of the microfluidic separation channel. A collection vessel may be in fluid communication with the first or second collection channel. The system may further be connectable to an intraluminal line. For instance, the system may be connectable to an intraluminal line configured to extract biofluid from a donor subject and deliver it to the source of the biofluid for processing. The system may be connectable to an intraluminal line configured to deliver an output suspension, for example target particle depleted fluid, to the recipient subject.

The system may further comprise a source of a target particle. The source of the target particle may be configured to deliver target particles to the biofluid for therapeutic treatment to the at least one component of the biofluid.

In some embodiments, the system further comprises a target particle processing chamber. The target particle processing chamber may be configured to unbind non-target particles from target particles prior to separation. In some embodiments, the target particle processing chamber is fluidly connected to a source of a treatment fluid configured to facilitate detachment of the non-target particles from the target particles.

According to certain embodiments, the system further comprises a recycle line. The recycle line may be configured to deliver output suspension back to the source of the biofluid for a second pass separation. The output suspension may be target particle enriched fluid or target particle depleted fluid. The recycle line may be configured to recycle target particle depleted fluid from the second outlet to the source of the biofluid. In some embodiments, the system comprises more than one microfluidic separation channel arranged in series.

In accordance with another aspect, there is provided a kit for separation of target particles from non-target particles. The kit may comprise at least one microfluidic separation channel connected to an acoustic transducer, a source of an additive fluidly connectable to the at least one inlet of the microfluidic separation channel, and instructions for use.

The kit may include instructions to collect a biofluid, introduce target particles into the biofluid to provide a therapeutic treatment to at least one component of the biofluid, pretreat the biofluid by introducing a predetermined volume of additive into the source of the biofluid, flow the pretreated biofluid through the microfluidic separation channel, and apply acoustic energy to the separation channel. In some embodiments, the kit provides instructions to introduce the additive to alter or regulate the density of the biofluid or concentration of the target particles or non-target particles.

According to certain embodiments, the kit may further comprise a collection channel, a collection vessel, a manifold system, a sensor, a control module, or an intraluminal line.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 is a micrograph of a microfluidic separation channel coupled to an acoustic transducer that is turned on;

DETAILED DESCRIPTION

Figure 1:
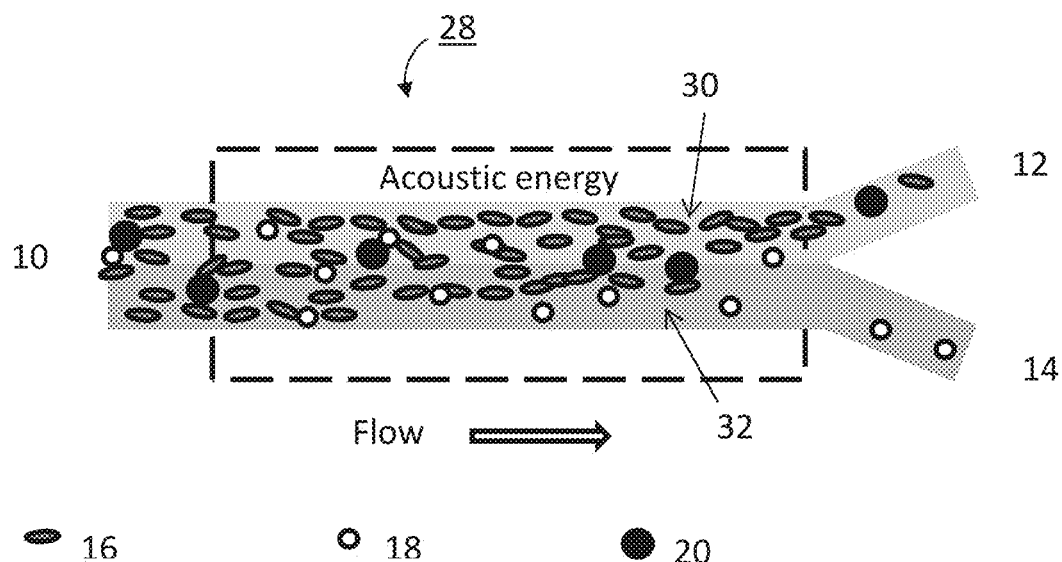
FIG. 1 is a schematic drawing of a microfluidic separation channel, according to one embodiment.

In the fields of bioprocessing and cell therapy emerging medical techniques may involve use or introduction of a particle into a biofluid sample for therapeutic treatment. The therapeutically treated or engineered biofluid sample may be introduced into a patient to medical treatment. In many applications, the particle may be a foreign particle that is not desirably introduced into a patient.

For instance, cell therapy and bioprocessing methods may involve extraction of blood or tissue from a patient followed by purification of a particular cell type from a sample. In some applications, the particular cell type is prepared for treatment or manipulated before it is re-injected into a patient. In certain applications, the particular cell type is identified with a capture particle. After processing, the cell type may be detached from the capture particle, leaving a suspension of capture particles and cells in the fluid. Aspects and embodiments disclosed herein relate to separation of used capture particles from a liquid suspension of mixed cells and particles. In particular, one example application is the separation of synthetic cell capture particles from a blood sample. For instance, synthetic capture particles with surface CD3+, CD4+, or CD8+ antibodies designed to selectively bind T-lymphocytes from a blood sample.

In another exemplary application, magnetic processing of cells can be highly selective, but depends on the attachment of paramagnetic capture particles to cells using affinity ligands, such as antibodies. The particles may pose a safety risk if injected into a patient. Accordingly, the magnetic particles must be removed from a final therapeutic product.

Aspects and embodiments disclosed herein may relate to methods and systems for use in processing of cells for cell therapy. Many other uses of some of the embodiments described herein could also be envisioned, in particular wherever a foreign particle is desired to be introduced into a biofluid to provide a therapeutic treatment, and then collected from the biofluid sample after treatment. Some non-limiting examples include the diagnostic or environmental monitoring assays, tissue engineering, in vitro models, and biomanufacturing systems, such as for energy applications.

Formerly washing of biofluid samples to remove foreign particles has been performed by one or more batch centrifugations, continuous centrifugations, magnetic separation, or combinations thereof. Centrifugation is only able to separate particles by density, limiting its ability to separate particles from similarly dense cells. Addition of a density medium may improve particle separation, but only in small batch procedures requiring technically trained operators.

Membrane based filtration may be partially successful in removing foreign particles from a suspension sample, but difficulties persist. Generally, membrane based filtration provides only size exclusion of particles. Foreign capture particles may be essentially similar in size to desired cells, creating difficulty in selectively separation foreign particles from a cell suspension.

Aspects and embodiments disclosed herein may be advantageous over previous sample purification technologies because, for example, in some embodiments the removal of particles can be performed continuously, in some embodiments, the systems and methods provide separation by both size and density to further enhance particle separation, in some embodiments the separation processes may be readily scaled to small or large sample volumes, in some embodiments, a high degree of purification can be achieved with the addition of safely injectable, physiologically acceptable additives.

One non-limiting example application of the methods and systems disclosed herein is large scale bioprocessing. In some bioprocesses cells, such as mesenchymal stem cells, may be cultured on carrier particles. The carrier particles may be suspended in a medium and provide a substrate needed for cell development. Before the cultured cells may be used in therapies or research, they must be detached from the carrier particles, for example by biochemical separation. The detached carrier particles must be removed from the suspension to harvest the final cell product.

The aspects and embodiments disclosed herein may improve methods for selectively separating target particles from a biofluid, and may also have applications in other steps in the process such as purification of samples after transduction.

Acoustic separation, also referred to as acoustophoresis, may be used to isolate or enrich desired cells as part of a bioprocessing workflow. Acoustic separation of particles in a biofluid has been described in, for example, U.S. Patent Application Publication Nos. 2016-0030660, 2016-0008532, and 2013-0048565, and in U.S. Pat. No. 9,504,780, each of which is herein incorporated by reference in their entirety. The aspects and embodiments disclosed herein provide separation of a target particle from a liquid suspension of mixed cell types including other non-target particle types. More specifically, the aspects and embodiments disclosed herein provide improved selective separation of target particles from a biofluid suspension by introducing a physiologically acceptable additive to alter one or more physical properties of the fluid, target particle, or non-target particles.

In acoustic separation, a mixed suspension may flow through a duct that is oscillated at ultrasonic frequencies by an external mechanical oscillator. The duct may form a resonant cavity, for instance so that ultrasonic pressure waves are generated and contact the flow across the duct. For example, the ultrasonic waves may be generated at an angle relative to the flow. Ultrasonic waves may be generated in a direction substantially transverse to the flow. Cells or other particles in the suspension may experience a force from the pressure waves and migrate to nodes in the resulting pressure field. The rate at which particles migrate generally depends on their size, density, and compressibility. Separation may be facilitated, for example, by larger and more dense particles migrating to a pressure node, with smaller or neutrally buoyant particles migrating slowly, not migrating (substantially staying on axis), or migrating to anti-nodes. For instance, in a typical configuration separation process, the pressure node is established along the axis of the duct and certain particles may move to this pressure node axis and flow in a concentrated stream along it, while other particles may remain disperse or move to a pressure anti-node axis.

Referring again to the example application of large scale bioproces sing, carrier particles may be preferentially extracted from cell culture samples. The separation may involve altering a property of the cell culture suspension, of the carrier particles, or of a certain class of cells within the suspension, such that the carrier particles are less susceptible to acoustic energy than, for example the stem cells and other classes of cells. Therefore, when a biofluid, for example a cell culture suspension, is passed through an acoustic separator, carrier particles may remain in a side stream with greater abundance than the desired cells. The side stream may be discarded or collected for processing and the center stream may be collected. Conversely, the separation may involve altering a property of the carrier particles to make them more susceptible to the acoustic energy. For instance, iron nanoparticles may be added to a polymeric carrier particle. In other embodiments, the carrier particle may comprise a polymer of higher density or lower compressibility than the class of cells cultured.

In certain embodiments, the carrier particle may be designed or engineered to provide a modified carrier particle having properties that further enhance separation from target cells. For instance, the particle material may be modified or engineered to facilitate separation from the target cells, or the particle may comprise a filler that is designed, modified, or engineered to have specific properties that facilitate separation from the target cells.

In accordance with an aspect, there is provided a method of separating target particles from non-target particles in a biofluid. More specifically, there is provided a method for selective, differential separation of a desired particle from a biofluid comprising a suspension of mixed cell types and other particles. Target particles which may be selectively separated from the mixed cell types and other particles in the suspension include synthetic particles, carrier particles, capture particles, enrichment particles, delivery particles subclasses thereof, and combinations thereof. For instance, in some embodiments, target particles are capture particles configured to bind a therapeutic moiety, a toxin, a desired cell type, or a synthetic particle. In some embodiments, target particles are carrier particles configured to culture stem cells. In some embodiments, target particles are configured to deliver a therapeutic moiety.

Generally, target particles may be foreign particles introduced into the biofluid to provide a therapeutic treatment. The therapeutic treatment may comprise delivering a therapeutic moiety, capturing a non-target particle, enriching the biofluid for a non-target particle, or culturing a cell type. The therapeutic moiety may comprise a drug, a chemically active substance, or a biologically active substance. The target particles may be configured to capture non-target particles for separation or enrichment in the biofluid. As previously described, the target particles may be cell culture carrier particles configured to culture stem cells.

Non-target particles may comprise any and all particles in the biofluid not selected as the target particle. Generally, non-target particles may comprise plasma, proteins, bacteria, toxins, viruses, cells, or other biochemical particles. Non-target particles may comprise cells selected from the group consisting of erythrocytes, platelets, granulocytes, monocytes, macrophages, leukemic cells, and leukocytes. In some embodiments, the non-target particles are platelets and erythrocytes.

Target particles may be approximately the same size as certain cells. In order to separate target particles from cells in a biofluid, efficiency may be greatly increased by including an additive to alter or regulate at least one parameter of the biofluid. For instance, the additive may alter the aggregation potential of non-target particles and/or the density of the biofluid. According to certain embodiments, the additive is introduced in sufficient volume to regulate the density of the biofluid to be substantially similar to the density of the target particles.

According to certain embodiments, target particles are separated from non-target particles and removed to produce a target particle depleted fluid. The non-target particles may comprise live cells, frozen cells, preserved cells, or cells grown in a cell culture. The target particle depleted fluid may comprise a lower concentration of target particles, as compared to the biofluid suspension, the biofluid treated with target particles, or the pretreated biofluid.

Generally, a biofluid, for example whole blood, comprises a high concentration of erythrocytes. To produce a target particle depleted fluid, it may be desirable to selectively separate erythrocytes from the target particles.

The method of separating target particles from non-target particles in a biofluid may further comprise providing a biofluid. In some embodiments, the biofluid may be obtained from a donor subject. The donor subject's biofluid may be subjected to down-stream processes directly, or may be collected and stored for later processing. As used herein, "directly" refers to processing of the biofluid without subjecting the biofluid to a long-term storage period. For instance, the biofluid may be processed immediately in an in-line arrangement, within minutes, or within hours. The biofluid may be stored for one day or more.

In some embodiments, the biofluid is collected from a donor subject through an intraluminal line. Accordingly, the method may further comprise obtaining the biofluid from a donor subject through an intraluminal line. As used herein, an "intraluminal" line refers to a transfusion line connectable to a lumen of a subject. More specifically, an intraluminal line may be connectable to a body cavity, tubular structure, or organ in the body, such as a vein, an artery, the bladder, or intestine. For instance, a transfusion line may be connectable to the circulatory or gastrointestinal system of the subject. The intraluminal line includes, for example, intravenous lines, central venous lines, intravascular lines, intratissue lines, catheters, and transfusion lines. The intraluminal line catheter may be, for example, a peripheral indwelling catheter, an intravenous catheter, or a central venous catheter.

As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

In accordance with certain embodiments, the biofluid may be obtained from a standard blood processing device. For instance, the biofluid may be obtained from an apharesis machine. The biofluid may be directly obtained from a standard blood processing device and further processed immediately, for example in an in-line arrangement. In other embodiments, the biofluid may be obtained from a standard blood processing device and stored for one day or more before being introduced into the microfluidic separation chamber.

In some embodiments, the method further comprises selecting the biofluid from blood buffy coat, leukapheresis product, peripheral blood, whole blood, lymph fluid, synovial fluid, spinal fluid, bone marrow, ascities fluid, and combinations or subcomponents thereof. The biofluid may comprise a synethetic medium comprising a cell suspension. For instance, the biofluid may comprise a cell culture medium. In some embodiments, the biofluid may comprise a subcomponent of a biofluid. For instance, the biofluid may comprise cell enriched biofluid, cell depleted biofluid, diluted biofluid, concentrated biofluid, filtered biofluid, purified biofluid, or otherwise treated biofluid.

As used herein, leukapheresis product refers to a blood product which has undergone an apheresis separation process. The apheresis separation process may have been performed to deplete or enrich for leukocytes. Thus, the leukapheresis product may comprise leukocyte enriched apheresis product or leukocyte depleted apheresis product. In some embodiments, the leukapheresis product may comprise synthetic biofluid. In some embodiments, the leukapheresis product may be purchased from a manufacturer. In some non-limiting embodiments, the leukapheresis product is LeukoPak™ leukapheresis product, as distributed by AllCells (Alameda, CA).

According to certain embodiments, the method may further comprise introducing target particles into the biofluid. In some embodiments, the target particles may be introduced after the biofluid is collected and before further processing, according to the methods described herein. The target particles may be introduced in-line, upstream from the pretreatment of the biofluid with an additive. The biofluid comprising target particles may be processed or stored for a period of time before introducing the additive into the biofluid.

In some embodiments, the biofluid may comprise target particles bound to non-target particles. Such an embodiment is envisioned, for example, when the target particles comprise carrier, capture, delivery, or enrichment particles. The method may further comprise detaching the non-target particles from the target particles before separation within the fluid. For instance, the method may comprise treating the biofluid to unbind the non-target particles for separation. The biofluid may be treated with a biochemical additive capable of unbinding the non-target particles. The biofluid non-target particles may be unbound from the target particles physically, for example by releasing a magnetic force.

The method of separating target particles from non-target particles in a biofluid may further comprise pretreating the biofluid. In some embodiments, pretreating the biofluid comprises introducing an additive into the biofluid to alter at least one of size of the target particles, size of the non-target particles, compressibility of the biofluid, compressibility of the target particles, compressibility of the non-target particles, aggregation potential of the target particles, and aggregation potential of the non-target particles. The method may further comprise introducing an additive into the biofluid to alter at least one of density of the biofluid, density of the target particles, density of the non-target particles. The additive may be cell-friendly. For instance, in some embodiments, the concentration of additive introduced into the biofluid is generally safe for intraluminal injection into a subject. In some embodiments, the additive selected is physiologically acceptable and generally safe for intraluminal injection into a subject.

Generally, the method may comprise introducing an additive to modify the biofluid or particle chemistry, to enhance separation of target particles from non-target particles. For instance, the biofluid's electrolyte concentration (i.e. salinity or tonicity) may be adjusted, such that the particle or a desired cell type is enlarged, swollen, crenated, sphered, or rigidified in response. For instance, the change in one or more physical properties of the non-target particle cell type may affect the response of the cell to the applied acoustic force within the microfluidic separation channel, enabling a differential separation between the target particle and other non-target particles, including cell types within the biofluid. The method may comprise selecting the additive from the group consisting of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

The method may comprise introducing an additive to alter size or shape of the target particles or non-target particles. As previously mentioned, a target particle or non-target particle may become swollen, crenated, sphered, or rigidified in response to the introduction of an additive in the biofluid. The change in size or shape may facilitate discrimination between the particles in the separation process. An additive may also be introduced to activate a desired non-target particle cell type, whereby, for example, an activated cell may be larger than a target particle. Thus, natural morphological changes due to biochemically induced activation or the natural cell cycle may be exploited to separate target particles from non-target particles.

The method may comprise introducing an additive to alter sodium or ion concentration of the biofluid. For instance, a concentrated sodium chloride solution may be introduced to crenate and/or shrink erythrocytes and other non-target particles by osmosis. Without wishing to be bound by a particular theory, it is believed that hemoglobin contained within erythrocytes will effectuate an increase in density simultaneously with a decrease in volume of the cell. Thus, it may be possible to selectively increase the density of erythrocytes by decreasing their size, to promote an enhanced separation of target particles from non-target particles, including erythrocytes.

In some embodiments, the method comprises introducing an additive to alter compressibility of the biofluid, target particles, or non-target particles. For instance, detergents and/or surfactants may be added to alter cell membrane mechanics, such that desired non-target particle cell types undergo a change in compressibility. In some embodiments, detergents or surfactants alter the cell membrane, such that desired non-target particle cell types are more susceptible to changes in ion concentration in the biofluid.

An additive may be introduced into the biofluid to alter aggregation potential of the target particles or the non-target particles. As used herein, "aggregation potential" refers to the mechanism by which a desired cell type or particle aggregates, agglutinates, adheres, or forms a complex with like particles. In some embodiments, the aggregation potential refers to a desired cell type's ability to aggregate with cells of the same or a different cell type. For instance, an additive may be introduced to alter or regulate the aggregation potential of erythrocytes or platelets. Generally, many biofluids comprise a high concentration of erythrocytes and/or platelets. By aggregating the erythrocytes and/or platelets, a more efficient separation from target particles may be achieved.

In some embodiments, the aggregation potential is altered or regulated by an additive that prohibits a target particle, non-target particle, or a desired cell type from binding, aggregating, agglutinating, adhering, or forming a complex with a like or different particle. For instance, the aggregation potential may be altered or reduced by an anti-coagulant. In other embodiments, the aggregation potential may be altered, enhanced, or regulated by a cell aggregator. As used herein, a "cell aggregator" refers to an additive that may bind, aggregate, adhere, agglutinate or form a complex with a desired cell type. A "cell aggregator" may also refer to an additive that may cause a desired cell type to bind, aggregate, adhere, agglutinate, or form a complex with like or different cell types. The cell aggregator may cause cells to aggregate by activating natural biochemical pathways, by altering cell mechanics, or by reducing or screening electrostatic barriers between cells in the pretreated biofluid.

In some embodiments, the method further comprises selecting the cell aggregator to be a long-chain polysaccharide. Long-chain polysaccharides include, but are not limited to, dextran, polysucrose, hetastarch (hydroxyethyl starch), and Ficoll™ media, distributed by GE Healthcare (Chicago, IL). The long-chain polysaccharide may have a molecular weight between about 100 kD and about 500 kD. In some embodiments, the long-chain polysaccharide has a molecular weight between about 250 kD and about 500 kD, between about 200 kD and about 400 kD, between about 300 kD and about 400 kD. The long-chain polysaccharide may have a molecular weight of about 100 kD, about 200 kD, about 250 kD, about 300 kD, about 400 kD, and about 500 kD. In some embodiments, the cell aggregator comprises a long-chain polysaccharide present at a concentration of between about 0.5% (w/v) and about 25% (w/v). In some embodiments, the cell aggregator comprises a long-chain polysaccharide present at a concentration of between about 1.0% (w/v) and about 20% (w/v), between about 5.0% (w/v) and about 15% (w/v), between about 8.0% (w/v) and about 12% (w/v). For instance, the cell aggregator may comprise a long-chain polysaccharide present at about 0.5% (w/v), about 1.0% (w/v), about 2.0% (w/v), about 5.0% (w/v), about 8.0% (w/v), about 10% (w/v), about 12% (w/v), about 15% (w/v), about 20% (w/v), about 24% (w/v), and about 25% (w/v).

In some embodiments, the method further comprises selecting the cell aggregator to be a platelet aggregator or a cell adhesion molecule (CAM). The CAM may be released or obtainable from an activated platelet granule. Such CAMs aggregate platelets by known natural mechanisms. Platelet activation may induce the platelet to releases granules and exposed the contents of platelet granules on the outside of the cell. CAMs may then promote platelet aggregation through platelet-fibrin and platelet-platelet binding. CAMs may be released from an activated platelet granule by biochemically inducing their release, for example through activation by addition of thrombin, Type II collagen or adenosine diphosphate, or by introducing natural or synthetic CAMs obtained from a distributor into the biofluid. The CAMs released or obtainable from an activated platelet granule may include, but are not limited to, P-selectin and von Willebrand factor. Platelet activators include, but are not limited to, adenosine diphosphate, thrombin, Type II collagen, and ristocetin.

An additive may be introduced into the biofluid to alter density of the biofluid. In some embodiments, the additive is selected from a density gradient medium, a density additive, and combinations thereof. Density gradient media is a media for cell isolation, generally used in the practice of centrifugal separation. Density gradient media are well known in the art and include, for example, ACCUSPIN™ media, Histodenz™ media, OptiPrep™ media, and Histopaque® media distributed by Sigma-Aldrich (St. Louis, MO), Ficoll-Paque™ media and Percoll™ media distributed by GE Healthcare (Chicago, IL), RosetteSep™ media and Lymphoprep™ media distributed by STEMCELL Technologies (Vancouver, Canada). The list of density gradient media is merely exemplary and non-exhaustive. A density additive may comprise a reagent having a different density than the biofluid, or configured to regulate or alter the density of the biofluid. For instance, the density additive may comprise pure water, deionized water, a salt, a saline buffer solution, or a nonionic iodinated compound. Nonionic iodinated compounds include, but are not limited to, diatrizoic acid, meglumine diatrizoate, and iodixanol. According to certain embodiments, the density additive is selected to be cell-friendly, such that it does not increase osmolarity of the biofluid to a degree that would be harmful to the cells.

In some embodiments, the additive is introduced to alter or regulate the density of the biofluid to be within a range of the density of the target particles or non-target particles. The additive may be introduced to regulate the density of the biofluid to substantially match a density of the target or non-target particles. For example, the density may be regulated such that target particles approach neutral buoyancy in the biofluid, reducing the acoustic force acting on them, as compared to the force acting on the non-target particles. The density of the biofluid may be regulated to a density of between about 1.00 g/mL and about 1.15 g/mL. In some embodiments, the density of the biofluid is regulated to a density of between about 1.00 g/mL and about 1.10 g/mL, between about 1.10 g/mL and about 1.15 g/mL, between about 1.02 g/mL and about 1.09 g/mL, between about 1.03 g/mL and about 1.08 g/mL, between about 1.04 g/mL and about 1.07 g/mL, and between about 1.045 g/mL and about 1.065 g/mL. Specifically, the density of the biofluid may be regulated or altered to a density of about 1.00 g/mL, about 1.01 g/mL, about 1.02 g/mL, about 1.03 g/mL, about 1.04 g/mL, about 1.05 g/mL, about 1.06 g/mL, about 1.07 g/mL, about 1.08 g/mL, about 1.09 g/mL, about 1.10 g/mL, about 1.12 g/mL, and about 1.15 g/mL.

Pretreating the biofluid may further comprise introducing an additive to alter density of the target particles or non-target particles. The additive may be introduced to alter or regulate the density of biofluid and particles to be within a range of each other, for instance to make the particles approach neutral buoyancy within the fluid. A diluent, salt, or saline solution may be introduced to alter or regulate the density of target particles or non-target particles to illicit a certain response from a desired non-target particle cell type or to have a density within a range of the density of the biofluid. For instance, sodium or an ion concentration may be reduced, for example by dilution with deionized water, to swell a first type of particle by osmosis while other particles may use known natural mechanisms to regulate their size, increasing size discrimination between the two particle types. In another non-limiting example, erythrocytes swell more readily than target particles, and the additive may facilitate removal of the leukemic cells.

The method may comprise introducing an additive to alter both density of the biofluid and aggregation potential of the non-target particles. In some embodiments, the combination of a density additive and a cell aggregator produces a synergistic effect, whereby the method produces a more efficient separation of target particles from non-target particles and a higher concentration of target particles in the target particle enriched fluid than would be expected from the combination of both effects. For instance, in a method of separating target particles from leukocytes and erythrocytes, an additive or a combination of additives may be introduced to alter the density of the biofluid and to aggregate erythrocytes. The density additive may enhance the separation of the target particle, from the non-target particles (for example, the erythrocytes and leukocytes), while the cell aggregator may effectively increase the acoustic scattering radius of the non-target particles to enhanced separation of the non-target particles over the target particles. The individual additives, when used separately, may not provide sufficient separation of target particles from non-target particles including erythrocytes and leukocytes, but the combination may promote an enhanced effective differential separation of target particles from non-target particles.

In some embodiments the additive may further comprise affinity based capture particles. Generally, the affinity based particles are safe for intraluminal injection into a subject. For instance, the additive may comprise biochemical moieties, such as antibodies, that bind target particles or non-target particles. The cell aggregator may comprise a solution comprising antibodies that bind and aggregate target particles or non-target particles. In some embodiments, the antibodies bind and aggregate a desired target particle. The additive may comprise emulsion droplets, gel particles, or lipid encapsulated oil vesicles. In some embodiments, the affinity based capture particle is safe for intraluminal injection. The affinity based capture particle may be engineered to be "anti-focusing" or "positively focusing" by designing it with low density or high density. The low density "anti-focusing" capture particle may experience acoustophoretic forces in the opposite direction as the target particles or non-target particles. The high density "anti-focusing" capture particle may experience migration to the pressure anti-node, while target particles or non-target particles migrate toward the pressure node. In some embodiments, an acoustic analog to magnetic separation may comprise "positively focusing" capture particles. For instance, a "positively focusing" capture particle may be used to trap a desired target particle, such that selected non-target particles remain held in the separation channel, while other target particles flow through. The held non-target particles may be released at a later time. In some embodiments, a large capture particle molecule may bind to many points on the surface of a target particle, and may alter the acoustophoretic force exhibited on the particle by changing its effective diameter.

The method of separating target particles from non-target particles may further comprise flowing biofluid into an inlet of a microfluidic separation channel. For instance, the method may comprise flowing the pretreated biofluid into the microfluidic separation channel. The biofluid may have a flow rate of between about 0.03 mL/min to about 0.5 mL/min. In some embodiments, the biofluid may have a flow rate through the microfluidic separation channel of between about 0.05 mL/min to about 0.4 mL/min, about 0.1 mL/min to about 0.3 mL/min. The biofluid may have a flow rate through the microfluidic separation channel of about 0.03 mL/min, 0.05 mL/min, 0.08 mL/min, 0.1 mL/min, 0.2 mL/min, 0.3 mL/min, 0.4 mL/min, 0.5 mL/min, or any range therebetween.

The method may further comprise applying acoustic energy to the microfluidic separation channel. In some embodiments, the acoustic energy is applied in the form of an acoustic wave. The acoustic wave may be applied at an angle relative to the flow of fluid through the separation channel. The angle and magnitude of the acoustic wave may be engineered based on size of the device, size of the channel, or flow rate of fluid through the channel. In some embodiments, the acoustic energy may be applied in a direction substantially transverse to the biofluid flow through the microfluidic separation channel. The acoustic wave may be a standing acoustic wave. In some embodiments, the acoustic energy may be applied to the microfluidic separation channel continuously. The continuous application of acoustic energy may allow for a greater efficiency of separation. In alternate embodiments, the acoustic energy may be applied to the microfluidic separation channel intermittently or on a timed schedule. The intermittent energy application may allow for particles to move freely through the channel if there is a blockage.

The applied acoustic energy may act on the cells and particles within the biofluid to drive them according to size, density, and/or compressibility. In some embodiments, the method may comprise accumulating target particles within a primary stream along the separation channel. In some embodiments, the method may comprise accumulating non-target particles within a secondary stream along the separation channel. The accumulation of a target or non-target particle within a desired stream along the separation channel may be engineered by adjusting parameters such as wavelength, frequency, amplitude, power level, or other modulation of the applied acoustic energy.

Depending on the target particles or non-target particles selected according to the method, one class of particles may accumulate in response to a pressure node or anti-node generated by the acoustic energy. For instance, target particles may accumulate within a primary stream in response to a pressure node, and non-target particles may accumulate within a secondary stream in response to a pressure anti-node. Generally, particles, including cells, will be driven by the acoustic energy in response to their contrast factor. Particles may migrate at a rate which is proportional to the magnitude and sign of their contrast factors. In some embodiments, particles with a positive contrast factor are driven to pressure nodes, while particles with a negative contrast factor are driven to pressure anti-nodes. Particles with a greater magnitude contrast factor are generally driven at a faster rate than particles with a lesser magnitude contrast factor.

The rate at which particles are driven in response to their acoustic energy generally depends on particle size, density, and compressibility. Briefly, the contrast factor is based on the bulk modulus (K) and density ($\rho$) of a particle. When suspended in a fluid, the contrast factor ($\varphi$) for the particles is calculated with the below equation:

$$\varphi = \frac{5\rho - 2 \cdot 1.02}{2\rho + 1.02} + \frac{2.2}{K}$$

In some embodiments, the method of separating target particles from non-target particles in a biofluid comprises collecting the at least one primary stream comprising the target particles. Generally, the biofluid entering the microfluidic separation channel is a well-mixed primary stream, comprising desegregated target particles and non-target particles. Upon experiencing acoustic energy, target particles and non-target particles may generally accumulate into fractions of the general stream of biofluid. The fraction or fractions of biofluid flowing through the microfluidic separation channel selectively enriched in target particles are defined as the primary stream. There may be more than one fraction of biofluid within the microfluidic separation channel enriched in target particles. For instance, target particles may be driven to a pressure node at the center of the channel in one embodiment, and target particles may be driven to the pressure anti-nodes at the periphery of the channel in an alternate embodiment. The location of pressure nodes and anti-nodes within the channel may be designed by positioning the acoustic energy or by selecting frequency and wavelength of the acoustic waves. The primary stream comprising target particles may be collected for storage, for research, for recycling, or as waste Similarly, in some embodiments, the method of separating target particles from non-target particles comprises collecting the at least one secondary stream comprising non-target particles. The fraction or fractions within the biofluid selectively depleted in target particles, and selectively enriched in non-target particles are defined as the secondary stream. In certain embodiments, the target particles and non-target particles have opposing contrast factors. With opposing contrast factors, the target particles and non-target particles may be driven in opposite directions, or one may be driven away from the general stream, for example to the center or the periphery of the channel. In other embodiments, the target particles and non-target particles have contrast factors of a different magnitude, but the same sign. In these embodiments, one class of cells may be driven away at a faster rate than the other, defining the primary and secondary streams. The secondary stream may be collected for storage, immediate use, for transfusion into a subject, or for further research The method may comprise collecting the primary stream comprising target particles and further comprise separately collecting the at least one secondary stream comprising the non-target particles.

In some embodiments, the target particle enriched primary stream is collected for recycling target particles. Where the target particles are bound to other particles, the particles may be detached, as previously described, before recycling. The recycled target particles may be introduced into the biofluid, upstream from pretreating with an additive, to provide a therapeutic treatment to at least one component of the biofluid.

According to certain embodiments, target particle depleted fluid may be post-treated and delivered to a recipient subject. For instance, the secondary stream may be post-treated and delivered to a recipient subject. Post-treating a fluid may comprise a process such as washing, separating, concentrating, diluting, heating, purifying, or filtering capable of removing toxins, contaminants, or harmful chemical compounds from the fluid. In general, a fluid is post-treated to produce a physiologically acceptable fluid that may be directly delivered to a recipient subject, for example via an intraluminal line as previously described. The post-treated fluid may be stored for delivery to a recipient subject at a later time.

In some embodiments, the target particle depleted fluid is post-treated to produce a therapeutic fluid. Post-treating the fluid may comprise viral transduction, gene transfer, or gene editing of the target particles to produce a therapeutic, physiologically acceptable fluid for delivery to a recipient subject, as previously described.

In some embodiments, the recipient subject is the same as the donor subject. In other embodiments, the donor subject and the recipient subject are not the same. The donor subject and the recipient subject may generally be physiologically compatible.

The method may be performed in line such that the biofluid is collected from a subject, target particles are introduced into the biofluid to provide a therapeutic treatment, and the biofluid comprising target particles is directly pretreated, target particles are separated from non-target particles in the biofluid by a method as described herein to produce a target particle depleted fluid, the fluid depleted of target particles may be post-treated, and the post-treated fluid may be directly delivered back to the subject. In some embodiments, the method is performed essentially as previously discussed, however the target particles are separated from non-target particles to produce a target particle enriched fluid, which may be post-treated and delivered back to the subject.

According to certain embodiments, the method further comprises flowing a second fluid adjacent to the biofluid into an inlet of the microfluidic separation channel. The inlet may be an inlet separate from the biofluid inlet of the microfluidic separation channel. The biofluid and the second fluid may flow through the separation channel in substantially parallel form. For instance, both fluids may flow through the separation channel at opposite peripheries of the channel, the second fluid may flow through both peripheries of the channel, or the second fluid may flow in the center of the channel. The biofluid and the second fluid may flow through the separation channel in substantially laminar form. As used herein, substantially laminar flow includes substantially ordered flow. Laminar flow may have a Reynolds number (Re) less than about 2100. In certain embodiments, laminar flow has a Reynolds number (Re) less than about 4000.

In certain embodiments, the second fluid is an inert fluid that may comprise water, deionized water, or phosphate buffered saline (PBS). The second fluid may have its density adjusted with a density gradient medium or density additive, independently from the pre-treated biofluid. The applied acoustic energy may drive target or non-target particles from the biofluid into the essentially parallel flowing second fluid initially comprising no cells, such that the second fluid, now comprising selectively separated cells, may exit the microfluidic separation channel through a separate outlet. Where the target particles are driven into the second fluid, the second fluid comprising target particles is essentially the primary stream. Conversely, where the non-target particles are driven into the second fluid, the second fluid is essentially the secondary stream.

According to certain embodiments, the methods described herein may be performed in a staged separation or in series. Specifically a target particle enriched fluid or a target particle depleted fluid may be further processed by pretreating with an additive, flowing through a second microfluidic separation channel, and applying acoustic energy. The additive introduced into the fluid in the downstream operation may be the same or a different additive as the one introduced into the biofluid in the first pass separation process. Additionally, the target particles selected in the first pass process may be the same or different as those selected in the second pass process. As a non-limiting example, a biofluid may be pretreated and flowed through a microfluidic separation channel to produce a target particle depleted fluid. The output target particle depleted fluid may further be flowed through a second microfluidic separation channel to remove a different target particle. As another non-limiting example a biofluid may be flowed through a microfluidic separation channel to produce a selected cell type enriched fluid. The cell enriched fluid may be flowed through a second microfluidic separation channel to remove target particles and produce a further cell enriched fluid.

In some embodiments, the first pass target particle enriched or target particle depleted fluid is recycled and reintroduced into the biofluid or into the pretreated biofluid to flow through the microfluidic separation channel as a blend. For instance, the target particle depleted fluid may be recycled and reintroduced into the biofluid or pretreated biofluid to flow through the microfluidic separation channel a second time.

According to certain embodiments, the method further comprises dosing the at least one secondary stream comprising cells with a reagent to produce a dosed suspension. The at least one secondary stream may be a target particle depleted fluid. The reagent may be selected from an antigen or activation reagent configured to biochemically induce cell activation. The biochemically induced activation may allow for selection of subclasses of types of cells in a second pass separation, for instance lymphocytes or T cells, by exploiting the morphological changes of activated cells. In some instances, activated cells may be larger than non-activated cells and cell size may vary throughout the cell cycle. The difference in size may allow for differential separation of cells with acoustic energy.

The method may further comprise flowing the target particle depleted fluid comprising cells through a second microfluidic separation channel or through microfluidic separation channels arranged in series and applying acoustic energy to each separation channel. The dosed suspension may allow for selection of target particles at a certain stage of the cell cycle.

For instance, in some embodiments of the method, the target particle depleted fluid may comprise lymphocytes and the method may further comprise separating activated lymphocytes from non-activated lymphocytes in the secondary stream. The method may further comprise dosing the lymphocyte enriched fluid with a reagent to produce the dosed suspension, flowing the dosed suspension into an inlet of a second microfluidic separation channel, and applying acoustic energy to the second microfluidic separation channel. Activated lymphocytes may accumulate within at least one primary stream along the second separation channel and non-activated lymphocytes may accumulate within at least one secondary stream along the second separation channel.

In accordance with another aspect, there is provided a system for microfluidic particle separation. The system may be configured to separate target particles from non-target particles in a biofluid. In some embodiments, the system comprises at least one microfluidic separation channel comprising at least one inlet and at least one outlet. The at least one outlet may be a branched outlet, branching in a direction substantially away from the separation channel. In some embodiments, the microfluidic separation channel comprises a first outlet and a second outlet. The at least one inlet may be configured to receive biofluid and the at least one outlet may be configured to discharge the biofluid that has been subjected to acoustic energy. As the fluid flows through the microfluidic separation channel, it may be subjected to acoustic energy that drives the target particles and/or non-target particles towards pressure nodes and anti-nodes within the channel. In some embodiments, the first outlet is configured to discharge target particle enriched fluid and the second outlet is configured to discharge target particle depleted fluid.

The microfluidic separation channel may be formed of rigid materials. The rigid materials may have a high acoustic contrast with the biofluid. In alternate embodiments, the microfluidic separation channel may be formed of relatively elastic materials. The more elastic materials may have a lower acoustic contrast with the biofluid, however they may form good acoustic resonators that provide low acoustic impedance and provide relatively little wave energy loss in wave transfer. The materials to form the microfluidic separation channel may include silicon, glass, metals, thermoplastics, and combinations thereof. In some embodiments, the microfluidic separation channel may be formed of a thermoplastic material. The thermoplastic microfluidic separation channel may be small, disposable, relatively safer to handle than, for example, the glass or metal separation channels, and relatively less expensive to manufacture than the silicon, glass, or metal separation channels. In some embodiments, the thermoplastic microfluidic separation channels are manufactured by injection molding. The thermoplastic material may comprise polystyrene, acrylic (polymethyl methacrylate), polysulfone, polycarbonate, polyethylene, polypropylene, cyclic olefin copolymer, silicone, liquid crystal polymer, polyvinylidene fluoride, and combinations thereof. The microfluidic separation channel may be disposable.

In some embodiments, the microfluidic separation channel has a channel width of between about 0.2 mm to about 0.8 mm. The microfluidic separation channel may be about 0.2 mm, about 0.3 mm, about 0.4 mm, about 0.5 mm, about 0.6 mm, about 0.7 mm, or about 0.8 mm wide. In some embodiments, the microfluidic separation channel is between about 15 mm and about 35 mm long. The microfluidic separation channel may be about 15 mm, about 20 mm, about 25 mm, about 30 mm, or about 35 mm long. The microfluidic separation channel width may be correlated to the acoustic wave wavelength, such that each channel contains a pressure-node and/or pressure anti-node generated by the acoustic energy. The operating frequency may be chosen so that the acoustic wavelength in the fluid is about twice the width of the microchannel. In an exemplary embodiment the operating frequency is chosen so that the acoustic wavelength in the fluid is about 3-4 times the width of the microchannel.

The system may further comprise a source of biofluid in fluid communication with the microfluidic separation channel. The source of the biofluid may be a vessel or chamber in fluid communication with the at least one inlet of the microfluidic separation channel, configured to deliver biofluid to the separation channel. The source of the biofluid may be a mixing chamber configured to receive an additive or a second fluid to be introduced into the biofluid prior to flowing the biofluid through the microfluidic separation channel. The source of the biofluid may be heated, cooled, or mixed.

In some embodiments, the source of the biofluid is fluidly connected downstream of an intraluminal line, and configured to receive biofluid directly from a donor subject. The source of the biofluid may further be fluidly connected downstream to a biofluid sample, for instance a sample collected in a bag, vessel, tank, or other chamber.

The system may further comprise a source of a target particle. The source of the target particle may be configured to deliver target particles to the biofluid for therapeutic treatment to the at least one component of the biofluid. The source of a target particle may comprise a target particles suspended in a medium. The medium may be therapeutically active or may be inert. Generally, the medium may be physiologically acceptable for intraluminal injection.

In some embodiments, the system further comprises a target particle processing chamber. The target particle processing chamber may be configured to unbind non-target particles from target particles prior to separation. In some embodiments, the target particle processing chamber is fluidly connected to a source of a treatment fluid configured to facilitate detachment of the non-target particles from the target particles. For instance, the treatment fluid may comprise a biochemical additive, capable of detaching non-target particles from target particles. The biochemical additive may comprise a chemically active moiety or a biologically active moiety. The processing chamber may further be equipped with materials to physically detach non-target particles from target particles, for example by releasing a magnetic force.

In some embodiments, the system comprises a source of additive in fluid communication with the source of the biofluid, configured to introduce at least one additive into the biofluid. The additive contained in the source of the biofluid may be an additive capable of altering or regulating at least one of size of the target particles, size of the non-target particles, compressibility of the biofluid, compressibility of the target particles, compressibility of the non-target particles, aggregation potential of the target particles, and aggregation potential of the non-target particles, as previously discussed. The additive may further be capable of altering or regulating at least one of density of the biofluid, density of the target particles, density of the non-target particles. The source of the additive may be a chamber, vessel, or tank comprising the additive. In some embodiments, the system comprises more than one source of an additive, each source configured to introduce a separate additive into the biofluid. In some embodiments, the source of the additive may be heated, cooled, or mixed.

The system may further comprise at least one acoustic transducer coupled to a wall of the microfluidic separation channel. The acoustic transducer may be positioned to apply a standing acoustic wave transverse to the microfluidic separation channel. In some embodiments, the acoustic transducer is capable of emitting acoustic energy that drives cells and/or particles to a pressure node or anti-node. The acoustic transducer may comprise a piezoelectric vibrating element configured to emit acoustic energy. The denser and larger particles and cells may migrate towards the center of the separation channel in response to the acoustic energy emitted by the piezoelectric transducer. In some embodiments, the acoustic transducer is configured to emit acoustic energy between about 0.2 MHz and about 4.0 MHz. For instance, the acoustic transducer may emit acoustic energy between about 0.5 MHz and about 3.0 MHz or between about 0.5 MHz and about 1.5 MHz. The acoustic transducer may be configured to provide standing acoustic waves having a wavelength that is twice as long as the microfluidic separation channel width.

The microfluidic separation channel may further comprise one or more heat sinks configured to dissipate heat generated by the acoustic transducer. The heat sink may be configured to dissipate enough heat from the acoustic transducer to prevent the transducer from warming fluids flowing through the separation channel. In some embodiments, the heat sinks comprise thermoelectric coolers. In some embodiments, the system includes fluidic lines that flow into the heat sink to provide fluidic cooling to the heat sink.

Systems that comprise more than one microfluidic separation channel may comprise one acoustic transducer coupled to each microfluidic separation channel or one or more acoustic transducers coupled to a collection of microfluidic separation channels.

In some embodiments, the system comprises at least two microfluidic separation channels. The at least two microfluidic separation channels may be arranged in a parallel arrangement downstream of the source of the biofluid. In such embodiments, the system may further comprise a manifold configured to distribute biofluid to the at least two microfluidic separation channels. The manifold may be configured to receive a biofluid or pretreated biofluid sample and evenly distribute the sample to downstream microfluidic separation channels. In some embodiments, the manifold may be configured to continuously receive and distribute fluid, and in other embodiments the manifold may be configured to receive and distribute fluid in batches. The manifold configured to receive and distribute fluid in batches may be on a regular timer or may distribute fluid batches as it receives sufficient fluid.

In some embodiments, the manifold is configured to distribute the biofluid in response to the input biofluid load on the system. In some embodiments, the input biofluid load comprises between about 1 mL to about 10 L of fluid. In some embodiments, the input biofluid load on the system may have a flow rate of between about 0.1 mL/min to about 200 mL/min. Each microfluidic separation channel may be configured to receive flow rates of between about 0.1 mL/min to about 0.5 mL/min. The system may further comprise at least one sensor configured to measure an input biofluid load on the system. The input biofluid load sensor may be in electrical communication with the manifold, such that the manifold may distribute the biofluid to the two or more microfluidic separation channels in response to the measurement of the input biofluid load received from the input biofluid load sensor.

In some embodiments, the system further comprises at least one sensor configured to measure at least one parameter of the input biofluid. For instance, the biofluid sensor may be configured to measure at least one of density of the biofluid, HCT % of the biofluid, concentration of target particles, or concentration of non-target particles in the biofluid. In some embodiments, the biofluid sensor is configured to measure optical transmission or absorption of the biofluid at a predetermined optical wavelength. The at least one biofluid sensor may be positioned at the system input and configured to measure parameters from the input biofluid load, or may be positioned within the source of the biofluid and configured to measure parameters from the biofluid or pretreated biofluid. The system may further comprise a control module in electrical communication with the biofluid sensor. The control module may further be in electrical communication with the source of additive, and configured to introduce a predetermined volume of the additive into the biofluid in response to the measurement of the at least one parameter of the input biofluid.

In certain embodiments the additive is capable of altering or regulating at least one of density of the biofluid, density of the target particles, density of the non-target particles, and the predetermined volume of the additive is determined to alter or regulate the biofluid to have a desired density or concentration of target particles or non-target particles. For instance, the predetermined volume of the additive may be determined to allow target particles or non-target particles to approach neutral buoyancy in the biofluid. The predetermined volume of the additive may be determined to regulate the density of the biofluid to substantially match the density of the target particles or non-target particles. In some embodiments, the predetermined volume of the additive is determined to alter or regulate the density of the biofluid to a density of between about 1.00 g/mL and about 1.15 g/mL or to density ranges or values within this range, as previously discussed.

In some embodiments, the additive is capable of altering or regulating at least one of HCT % of the biofluid, concentration of the target particles, or concentration of the non-target particles, and the predetermined volume of the additive is determined to alter or regulate the HCT % of the biofluid to be less than about 10%. For instance, the predetermined volume of the additive may be determined to alter or regulate the HCT % of the biofluid to be less than about 30%, less than about 25%, less than about 20%, less than about 15%, less than about 10%, or less than about 5%.

According to certain embodiments, the system further comprises at least one sensor configured to measure a parameter of an output suspension. The output suspension may be target particle enriched fluid or target particle depleted fluid exiting the microfluidic separation channel through the at least one outlet, or product or waste exiting the system. The sensors may measure at least one of HCT %, concentration of target particles, or concentration of non-target particles in the output suspension. In some embodiments, the sensors may measure at least one of density of the output suspension, density of the target particles, density of the non-target particles, size of the target particles, size of the non-target particles, compressibility of the output suspension, compressibility of the target particles, compressibility of the non-target particles, and concentration of the additive in the output suspension. In some embodiments, the sensors may measure optical transmission or absorption of the output suspension at a predetermined wavelength.

The system may further comprise a control module in electrical communication with the output suspension sensor. The control module may be in electrical communication with the acoustic transducer, and configured to alter or regulate at least one input parameter of the acoustic transducer. For instance, the control module may alter or regulate the power, voltage, or frequency delivered to the acoustic transducer in response to a measurement of a parameter of the output suspension. The control module may further shut on or off the acoustic transducer in response to a measurement of a parameter of the output suspension. For instance, the control module may act in response to a measurement of HCT %, concentration of target particles, or concentration of non-target particles in the output suspension. The control module in communication with the output suspension sensor may be the same or different from the control module in communication with the biofluid sensor. In some embodiments, any control module may be designed to act in response to a measurement from any sensor within the system. For instance, the control module configured to introduce a predetermined volume of additive into the biofluid may further be in electrical communication with the output suspension sensor or input biofluid load sensor, and configured to act in response to a measurement received therefrom. In another embodiment, the control module configured to be in electrical communication with the acoustic transducer may also be in electrical communication with other sensors and configured to act in response to a measurement received from the biofluid load sensor or the biofluid sensor.

In some embodiments, the predetermined volume of the additive or the power, voltage or frequency delivered to the acoustic transducer are controlled to regulate the HCT % of the output suspension. For instance, the system may be controlled to provide an output suspension having a desired HCT % of less than about 20%, less than about 10%, or less than about 1%. In some embodiments, the HCT % of the output suspension is controlled to be less than about 10%, less than about 9%, less than about 8%, less than about 7%, less than about 6%, less than about 5%, less than about 4%, less than about 3%, less than about 2%, or less than about 1%. The desired output suspension HCT % will depend on the exact biofluid flowed through the system and the input biofluid HCT %. For example, if the input biofluid is whole blood having a HCT % of 45%, the system may be controlled to provide an output suspension having a HCT % of about 5%.

The system may further comprise a source of a second fluid in fluid communication with the at least one inlet of the at least one microfluidic separation channel. The source of the second fluid may be a vessel, tank, or chamber in fluid communication with the microfluidic separation channel, the source of the biofluid, or a line connecting the source of the biofluid with the at least one inlet of the microfluidic separation channel. The source of the second fluid may be configured to introduce the second fluid into the biofluid. In some embodiments, the biofluid and the second fluid flow in substantially parallel, substantially laminar flow, as previously discussed. The second fluid may be any fluid, as previously discussed.

In some embodiments, the system may further comprise a first and second collection channel in fluid communication with the at least one outlet of the microfluidic separation channel. The collection channel may be a fluid line configured to deliver output suspension to a vessel, recycle line, or fluidly connectable with an intraluminal line configured to deliver output suspension to a subject. A collection vessel may be in fluid communication with the first or second collection channel. The collection vessel may be used to store, freeze, heat, or otherwise keep output suspension.

According to certain embodiments, the system further comprises a recycle line. In some embodiments, the recycle line is a line or channel configured to deliver output suspension back to the source of the biofluid for a second pass separation. The recycle line may be configured to deliver output suspension back to the at least one inlet of the microfluidic separation channel. The output suspension that is recycled may be target particle enriched fluid or target particle depleted fluid.

The system may further comprise a recycle line configured to deliver target particle enriched fluid back to the biofluid to provide a therapeutic treatment to at least one component of the biofluid. The recycle line may be equipped with a target particle processing chamber to detach any non-target particles from the target particles, before delivering the target particles back to the biofluid. In some embodiments, the recycle line is equipped with a parallel system for microfluidic particle separation, as described herein.

In some embodiments, the system comprises a post-treatment chamber. The post-treatment chamber may be configured to post-treat output suspension to produce a post-treated fluid, physiologically acceptable fluid, or therapeutic fluid, as previously described.

The system may comprise one or more pumps to direct the biofluid through the system the one or more pumps may be an infusion pump configured to generate sufficient pressure to force the biofluid through the system. In some embodiments, the pump generates sufficient pressure to introduce the output suspension into the recipient subject through the intraluminal line.

The system may be connectable to more than one intraluminal line to produce an in-line system for separation of particles. For instance, the system may be connectable to an intraluminal line configured to extract biofluid from a donor subject and deliver it to the source of the biofluid for processing. The system may be connectable to an intraluminal line configured to deliver an output suspension, for example target particle enriched fluid or target particle depleted fluid, to the recipient subject. In some embodiments, the recipient subject may be the same as the donor subject, and the biofluid processing is performed in line and in real time.

In some embodiments, the system comprises more than one microfluidic separation channel arranged in series. The more than one microfluidic channel in series may be configured to separate target particles from non-target particles in consecutive separation channels to produce a fluid with a higher degree of target particle depletion. In some embodiments, the more than one microfluidic separation channel in series is configured to deliver target particle depleted fluid to downstream microfluidic separation channels. In alternate embodiments, the more than one microfluidic separation channel in series is configured to deliver target particle enriched fluid to downstream microfluidic separation channels. In some embodiments, the microfluidic separation channels in series are stacked to process relatively larger volumes of biofluid. The stacked configuration allows branched outlets of the separation channel to be easily connectable to branched inlets of a downstream separation channel.

In accordance with another aspect, there is provided a kit for separation of target particles from non-target particles. The kit may comprise at least one microfluidic separation channel connected to an acoustic transducer, a source of an additive fluidly connectable to the at least one inlet of the microfluidic separation channel, and instructions for use. The at least one microfluidic separation channel may be configured to separate target particles from non-target particles, as previously described herein. The source of the additive may be a vessel, chamber, or channel, as previously discussed herein and may comprise at least one additive, as previously discussed herein. The kit may further comprise any component of the system described herein, connectable to the microfluidic separation channel. For instance, according to certain embodiments, the kit may further comprise a collection channel, a collection vessel, a manifold system, a sensor, a control module, an intraluminal line, a pump, a source of a target particle, a target particle processing chamber, a post-treatment chamber, or fluid lines to fluidly connect the components of the kit.

The kit may comprise a collection channel fluidly connectable to one of the first outlet and the second outlet of the microfluidic separation channel. The kit may comprise a collection vessel fluidly connectable to the collection channel. The kit may comprise a collection channel fluidly connectable to the first outlet and configured to recycle target particle enriched fluid or target particle depleted fluid to the microfluidic separation channel or biofluid. The kit may comprise an intraluminal line fluidly connectable to one of the microfluidic separation channel and the first or the second outlet. The kit may comprise more than one microfluidic separation channel fluidly connectable to the source of the biofluid in parallel or in series. The kit may comprise one or more sensors or control modules connectable to the microfluidic separation channel.

The kit may include instructions to collect a biofluid, pretreat the biofluid by introducing a predetermined volume of additive into the source of the biofluid, flow the pretreated biofluid through the microfluidic separation channel, and apply acoustic energy to the separation channel. The kit may provide instructions to introduce a target particle into the biofluid to provide a therapeutic treatment to at least one component of the biofluid. The kit may further provide instructions to detach non-target particles bound to the target particles, for example, before introducing an additive into the biofluid.

In some embodiments, the kit provides instructions to introduce the additive to alter or regulate the density of the biofluid or concentration of the target particles or non-target particles. The kit may comprise instructions to introduce a predetermined volume of the additive to control a desired density of the pretreated biofluid, as previously discussed herein. For instance, the kit may comprise instructions to introduce the additive to regulate the density of the biofluid to a substantially match a density of the target particles or non-target particles. The kit may further comprise instructions to control the power, voltage, or frequency of the acoustic transducer to alter or regulate the HCT %, concentration of target particles or concentration of non-target particles in the output suspension, as previously discussed herein. For instance, the kit may comprise instructions to regulate the output suspension HCT % to be less than about 1%. The kit may comprise instructions to perform any step or collection of steps from the method of separating target particles from non-target particles.

The function and advantages of the embodiments discussed above and other embodiments of the invention can be further understood from the description of the figures below, which further illustrate the benefits and/or advantages of the one or more systems and techniques of the invention but do not exemplify the full scope of the invention.

As shown in the exemplary concept schematic drawing of FIG. 1, a biofluid comprising target particles 18 and non-target particles 16 and 20 is flowed through microfluidic separation channel 28, through the inlet 10. Acoustic energy is applied to the separation channel 28 within the illustrated dotted line rectangle. Acoustic energy may be applied by attaching a piezoelectric transducer (not shown) to one wall of the separation channel. Target particles 18 accumulate within primary stream 32 and exit the separation channel 28 through first outlet 14. Target particle enriched fluid exits the first outlet 14. Non-target particles 16 and 20 accumulate within secondary stream 30 and exit the separation channel through second outlet 12. The non-target particles 18 and 20 exit second outlet 12 in a non-target particle enriched fluid. In some embodiments, the target particle enriched fluid within the primary stream 32 is collected. In some embodiments, the non-target particle enriched fluid within the secondary stream 30 is collected.

Figure 2:
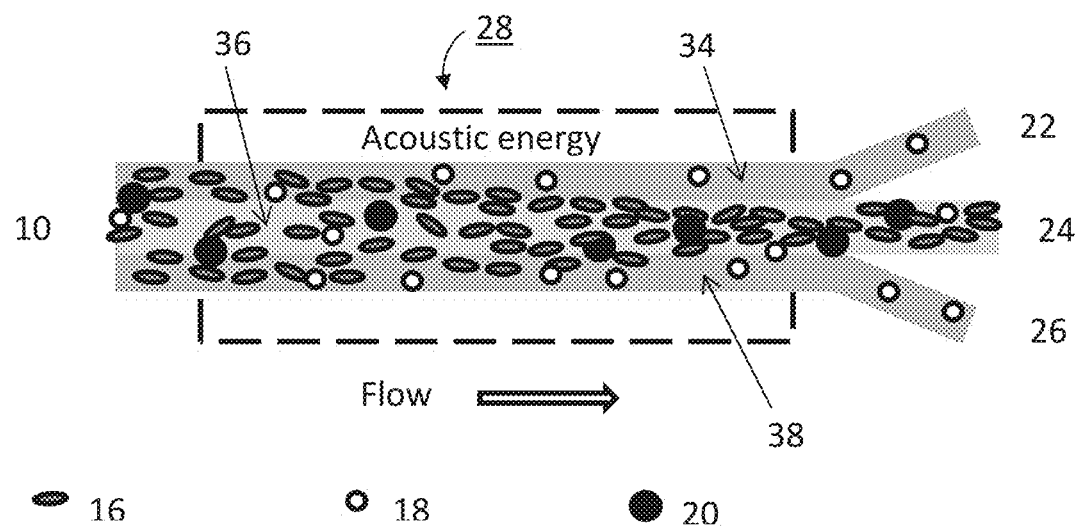
FIG. 2 is a schematic drawing of an alternate microfluidic separation channel, according to another embodiment.

Similarly, as shown in the exemplary concept schematic drawing of FIG. 2, the biofluid comprising target particles 18 and non-target particles 16 and 20 is flowed through the microfluidic separation channel 28 through inlet 10. In the embodiment exemplified in FIG. 2, target particles 18 essentially accumulate within two primary streams, 34 and 38, at the periphery of the separation channel 28, upon being subjected to the acoustic energy. Non-target particles 16 and 20 essentially accumulate within the central secondary stream 36. The primary streams 34 and 38 (target particle enriched fluid) exit the separation channel 28 through peripheral first outlets 22 and 26, while the secondary stream 36 (waste fluid) exits the separation channel 28 through second outlet 24. In this exemplary embodiment, non-target particles 16 and 20 are more susceptible to the acoustic energy, so they travel rapidly to the central region (secondary stream 36) of the separation channel 28, while the target particles 18 experience a weaker force from the acoustic energy and remain in the peripheral region of the separation channel 28 (primary streams 34 and 38).

Figure 3:
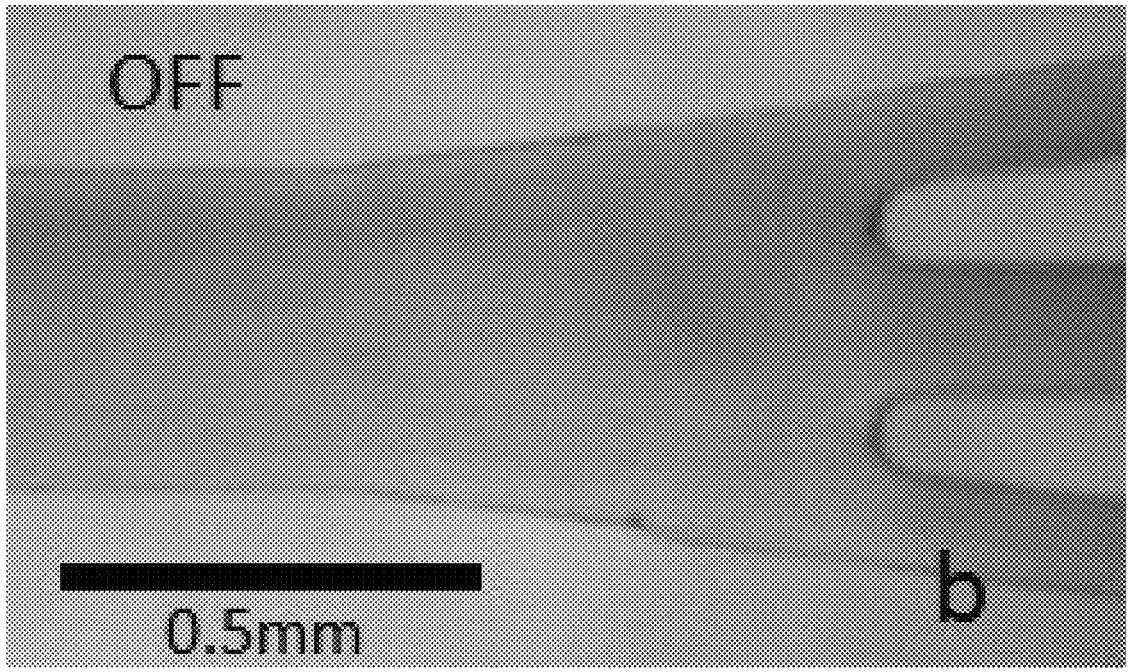
FIG. 3 is a micrograph of a microfluidic separation channel coupled to an acoustic transducer that is turned off.
Figure 4:
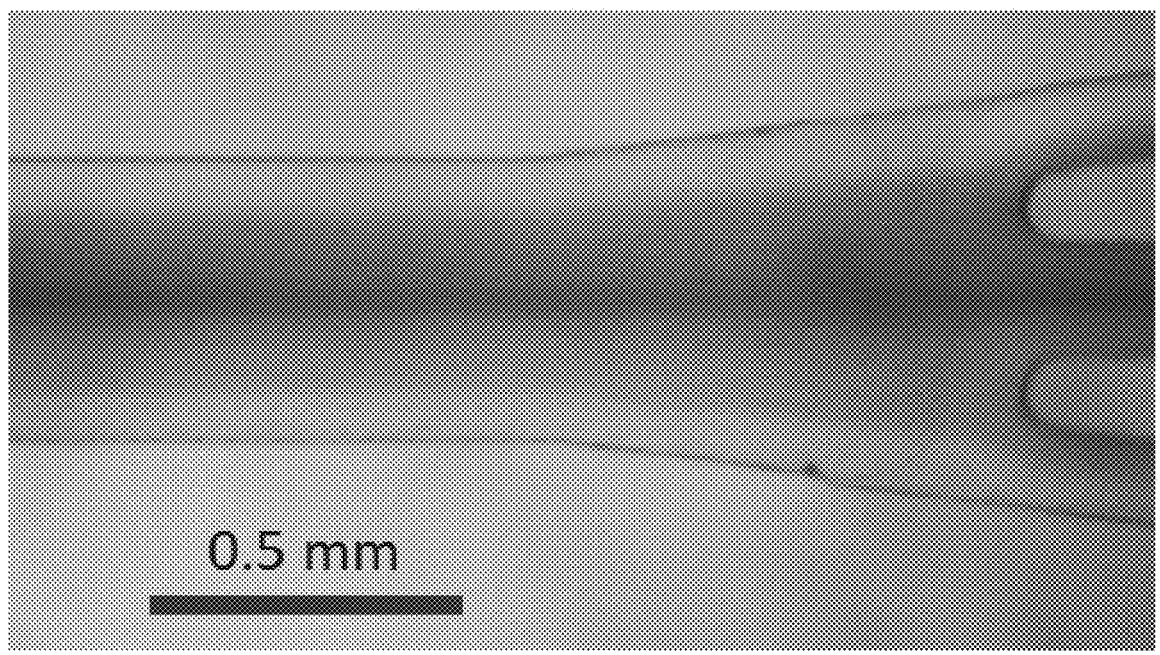

FIG. 3 and FIG. 4 are microscopic images of the downstream end of a microfluidic separation channel. In FIG. 3, the microfluidic separation channel is receiving no acoustic energy. As shown in the image, a homogeneous biofluid suspension is flowing through the channel with no separation. In FIG. 4, the microfluidic separation channel is receiving acoustic energy. Non-target particles, shown as the darker shade, can be seen traveling through the center stream, while target particles (not individually visible in the images) travel through the outer streams. The separation as seen in FIG. 4 is much greater than that seen in FIG. 3.

Figure 5:
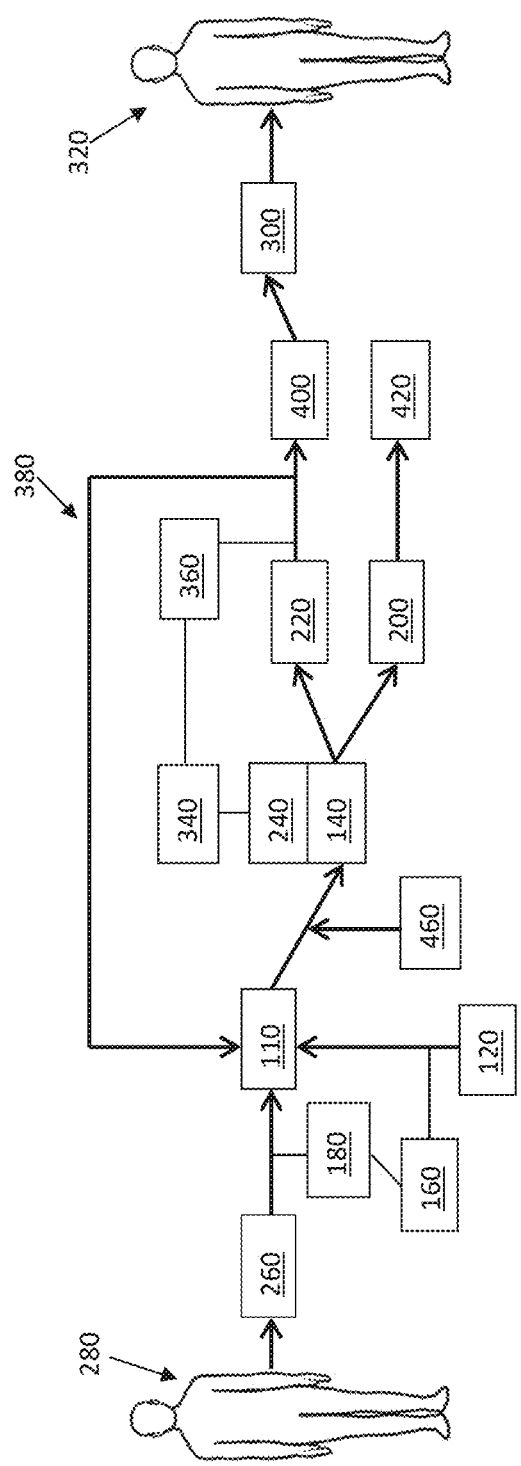
FIG. 5 is a schematic drawing of a system for microfluidic particle separation, according to one embodiment.

As shown in FIG. 5, according to certain embodiments, a system for microfluidic separation of target particles and non-target particles in a biofluid may comprise a source of a biofluid 110, a source of an additive 120, and a microfluidic separation channel 140 coupled to an acoustic transducer 240. The system may further comprise a sensor 180 configured to measure a parameter of an input biofluid and a sensor 360 configured to measure a parameter of a primary stream. In some embodiments, a sensor (not shown) is configured to measure a parameter of the secondary stream. The sensors may be electrically connected to control modules 340 and 160, such that control module 340 is configured to alter or regulate an input parameter of the acoustic transducer 240 and the control module 160 is configured to introduce a predetermined volume of the additive into the biofluid.

The system may further comprise intraluminal line 260 fluidly connected to donor subject 280 and second intraluminal line 300 fluidly connected to recipient subject 320. Recipient subject 320 and donor subject 280 may be the same subject. The microfluidic separation channel 140 may separate pretreated biofluid into a primary stream and a secondary stream, such that the primary stream comprising target particles (target particle enriched fluid) is directed to primary stream collection channel 200 and the secondary stream comprising non-target particles (target particle depleted fluid) is directed to secondary stream collection channel 220. The secondary stream 220 may be recycled back to the source of the biofluid 110 through recycle line 380 or may be post-treated in post-treatment chamber 400. In some embodiments, the post-treatment chamber 400 is fluidly connected to the intraluminal line 300. The primary stream 200 may be collected in collection vessel 420. The system may further comprise a source of a second fluid 460 fluidly connected to the microfluidic separation channel 140.

Figure 6:
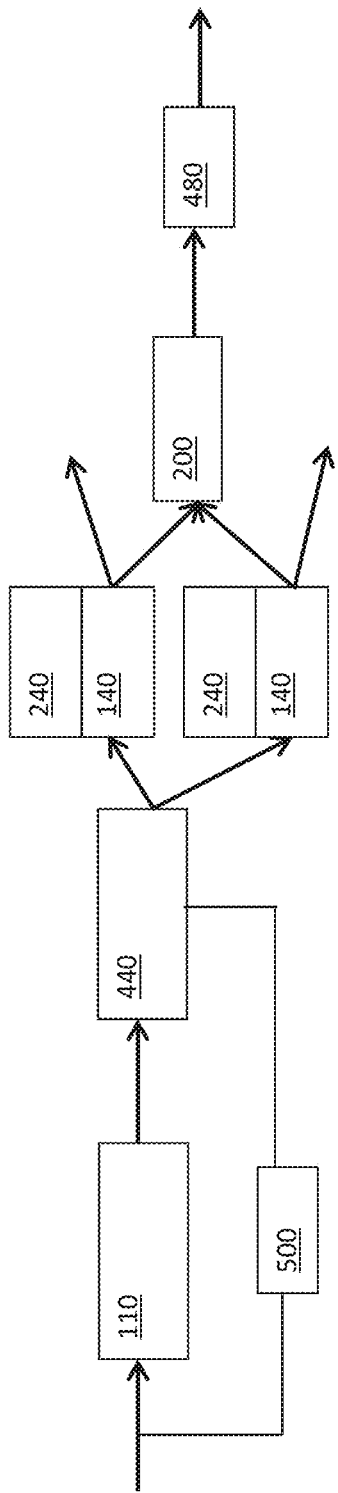
FIG. 6 is a schematic drawing of an alternate system for microfluidic particle separation, according to another embodiment.

Turning to FIG. 6, the system for microfluidic separation of target particles and non-target particles in a biofluid may further comprise two or more microfluidic separation channels 140. In the embodiment as shown, each microfluidic separation channel 140 is coupled to an acoustic transducer 240, however the system may comprise one acoustic transducer 240 coupled to more than one microfluidic separation channel 140. The two or more microfluidic separation channels 140 may be fluidly connected to a manifold 440, which may be fluidly or electrically connected to a sensor 500. The manifold 440 may be configured distribute the biofluid to the microfluidic separation channels 140 in response to a measurement received from the sensor 500 of an input biofluid load upstream of the biofluid source 110. In some embodiments, the system comprises a collection channel 200 downstream from the microfluidic separation channels 140 configured to collect the primary stream or secondary stream from the microfluidic separation channels 140. The system may further comprise a collection vessel 480 downstream from the collection channel 200.

Figure 7:
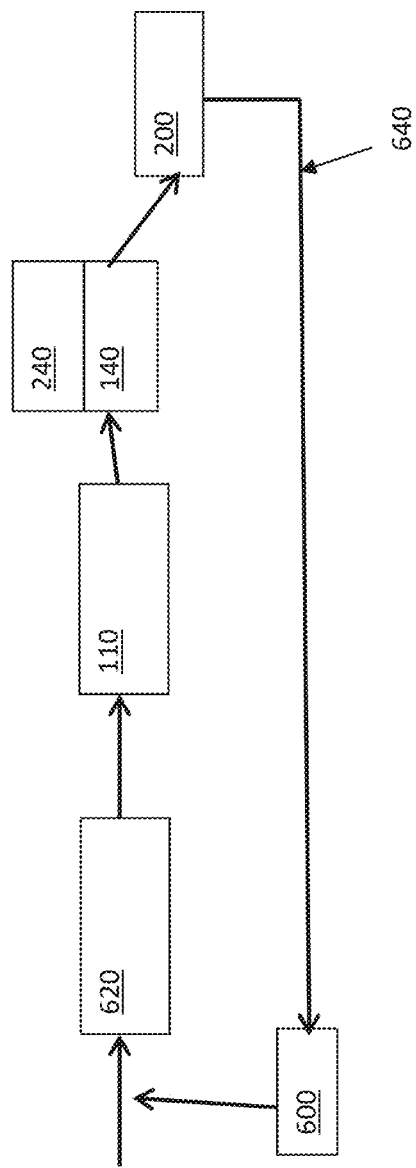
FIG. 7 is a schematic drawing of an alternate system for microfluidic particle separation, according to another embodiment.

The system may further comprise a source of a target particle 600, a target particle processing chamber 620, and a recycle line 640 configured to return target particles to the biofluid, as shown in the exemplary schematic diagram of FIG. 7.

Figure 8:
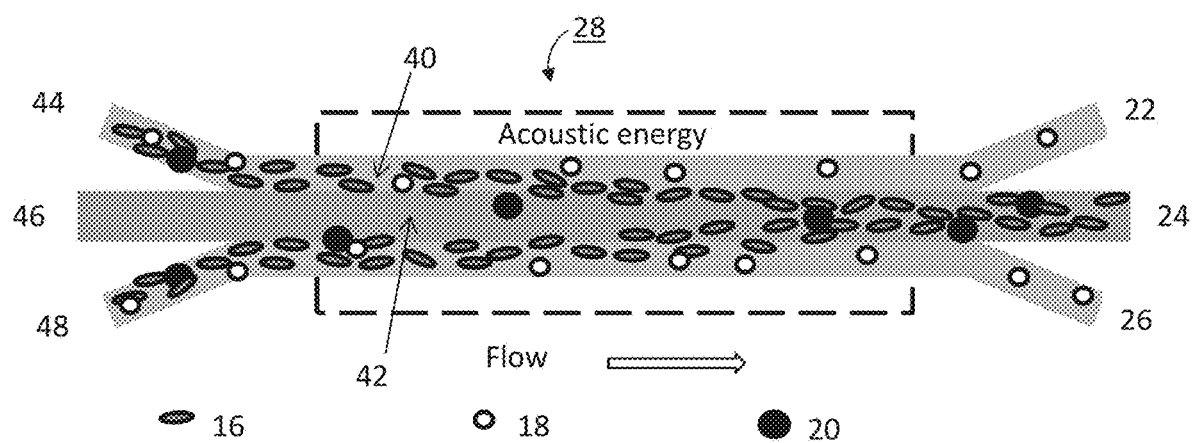
FIG. 8 is a schematic drawing of an alternate microfluidic separation channel, according to another embodiment.

As shown in exemplary concept schematic drawing of FIG. 8, a second fluid 42 may be flowed through the microfluidic separation channel 28 with pretreated biofluid 40, in essentially parallel flow. The second fluid 42 enters the microfluidic separation channel 28 through central inlet 46, while pretreated biofluid 40 enters the microfluidic separation channel 28 through peripheral inlets 44 and 48. The second fluid 42 does not comprise particles or cells as it enters the separation channel 28, and may be an inert fluid. Non-target particles 16 and 20 are driven towards the center stream by the applied acoustic energy, and exit the separation channel through waste outlet 24. Target particles 18 are essentially buoyant within the microfluidic separation channel 28, and are not driven to the central stream. The estimated recovery in the exemplary embodiment of FIG. 8 is calculated to be about 70%. Comparatively, the estimated recovery in an embodiment without introducing a second fluid, such as the one exemplified in FIG. 2, is about 65%.

EXAMPLES

Example 1

Prophetic Example of Acoustic Separation for Purification of Target Particles

Separation of target particles, for example cell culture carrier particles in a biofluid comprising mesenchymal stem cells, may be performed with a microfluidic separation channel. The mesenchymal stem cells may be collected from a human subject. Cell culture carrier particles are introduced into biofluid to culture the stem cells. After cell culture period, the cultured stem cells may be detached from the cell culture carrier particles by reaction with a biochemical additive. The biofluid comprising cultured stem cells and carrier particles must be processed to separate the carrier particles before the cultured stem cells may be introduced into a human subject.

The biofluid comprising stem cells and carrier particles is flowed through a microfluidic separation channel, for example, at a residence time of about 1 second. Ultrasonic waves may be applied to the channel to oscillate a portion of the channel having a cross section on the scale of the ultrasonic wavelength (~1 mm). The acoustic energy on the channel may be applied to drive the carrier particles toward an axial center stream.

The carrier particles and cultured cells may experience different acoustic forces. For example, the carrier particles may experience a weaker force than the cultured stem cells and other cells or particles within the biofluid. As the biofluid is flowed through the separation channel, the target particle enriched fluid, here the fluid comprising carrier particles, is accumulated along primary streams at the outside of the channel. The stem cell enriched fluid (comprising the non-target particles) is accumulated along secondary streams and separated by a branching in the channel. The stem cell enriched fluid is collected and analyzed. The carrier particle enriched fluid may be collected and washed for further use culturing cells.

Accordingly, target particle carrier particles may be separated from cultured stem cells and other non-target particles, according to the methods described herein.

Example 2

Prophetic Example of Acoustic Separation with an Additive

Biofluid comprising target particles and non-target particles may be subjected to acoustic energy, generally as described above. Prior to flowing the biofluid through a microfluidic separation channel, samples may be pretreated by diluting with an additive, for instance with a density gradient medium at diluent densities ranging between about 1.00 and 1.15 (g/mL). The results may be measured in separation ratio, a quantitative measurement of the ratio of target particles in the product (separation efficiency).

The separation Ratio for any subpopulation x, where "side" is the primary stream and "center" is the secondary stream $$SR_x = \frac{n_{x,side}}{n_{x,side} + n_{x,center}}$$

The fraction of the stream out the side channel (primary stream), also referred to as the flow split:

$$FR_{side} = \frac{V_{side}}{V_{center}}$$

The additive may provide efficient separation of target particles from other non-target particles. A maximum separation of target particles from other non-target particles may be effectuated near the density of the target particles.

Accordingly, target particle separation from non-target particles in a biofluid can be performed with superior results by pretreating the biofluid with an additive, such as a density gradient medium. Without wishing to be bound to a particular theory, it is believed particle separation by pretreatment with additives capable of altering density of the biofluid, density of the target particles, density of the non-target particles, size of the target particles, size of the non-target particles, compressibility of the biofluid, compressibility of the target particles, compressibility of the non-target particles, aggregation potential of the target particles, and aggregation potential of the non-target particles will provide superior results over no pretreatment because the rate at which the particles migrate generally depends on particle size, density, and compressibility relative to the density and compressibility of the suspending biofluid.

Example 3

Prophetic Example of Acoustic Separation with an Additive

Biofluid comprising target particles and non-target particles may be subjected to acoustic energy, generally as described above. Prior to flowing the biofluid through a microfluidic separation channel, samples may be pretreated by introducing a cell aggregator. For example, Ficoll™ PM 300 cell media (GE Healthcare, Chicago, IL), a long-chain polysaccharide may be introduced into the biofluid.

The samples pretreated with a cell aggregator may exhibit better non-target particle removal (for example, erythrocytes or cultured stem cells) than the samples that were not pretreated Both the cell aggregator samples and the density gradient medium samples, as described above, may exhibit improved non-target particle removal and target particle recovery than control samples pretreated with PBS alone.

It is expected that, pretreating the biofluid with a cell aggregator will provide superior non-target particle removal, but inferior target particle recovery, than pretreating the biofluid with a density gradient medium. Furthermore, non-target particle separation from target particles in a biofluid can be performed with superior results by pretreating the biofluid with a density gradient medium and a cell aggregator, as compared to pretreating the biofluid with either additive individually or PBS alone.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for microfluidic particle separation. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure, and are intended to be within the spirit and scope of the disclosure. In other instances, an existing facility may be modified to utilize or incorporate any one or more aspects of the methods and systems described herein. Thus, in some instances, the systems may involve microfluidic particle separation. Accordingly the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the following claims.

What is claimed is:

1. A method of separating target particles from non-target particles in a biofluid, the method comprising:
   providing the biofluid comprising the target particles and the non-target particles, the target particles being unbound;
   introducing into the biofluid an additive to regulate the density of the biofluid while preserving the integrity of the particles, wherein the density of the biofluid is regulated to substantially match a density of the target particles;
   flowing the pretreated biofluid into an inlet of a microfluidic separation channel; and
   applying acoustic energy to the pretreated biofluid within the microfluidic separation channel, such that the target particles accumulate within at least one primary stream along a peripheral region of the microfluidic separation channel and the non-target particles accumulate within at least one secondary stream along a central region of the microfluidic separation channel to separate the target-particles and the non-target particles, the separation occurring within the microfluidic separation channel; and
   continue flowing the at least one primary stream and at least one secondary stream within the microfluidic separation channel along a same axis towards an outlet opposite the inlet.

2. The method of claim 1, further comprising collecting the at least one primary stream comprising the target particles.

3. The method of claim 2, further comprising separately collecting the at least one secondary stream comprising the non-target particles.

4. The method of claim 1, further comprising selecting the additive from the group consisting of a cell aggregator, deionized water, a detergent, a surfactant, a solution to regulate salinity of the biofluid, a solution to regulate tonicity of the biofluid, a solution to regulate viscosity of the biofluid, a solution to regulate osmolarity of the biofluid, a solution to regulate ion concentration of the biofluid, and combinations thereof.

5. The method of claim 4, further comprising selecting the cell aggregator to be a long-chain polysaccharide.

6. The method of claim 5, wherein the cell aggregator comprises a long-chain polysaccharide having a molecular weight between 100 and 500 kD.

7. The method of claim 5, wherein the cell aggregator comprises a long-chain polysaccharide present at a concentration of between about 0.5% (w/v) and about 25% (w/v).

8. The method of claim 4, further comprising selecting the cell aggregator to be a solution comprising antibodies that bind and aggregate non-target particles.

9. The method of claim 4, further comprising selecting the cell aggregator to be a platelet activator or a cell adhesion molecule.

10. The method of claim 1, further comprising selecting the additive from the group consisting of a density gradient medium, a density additive, and combinations thereof.

11. The method of claim 10, further comprising selecting the density additive to be a nonionic iodinated compound.

12. The method of claim 1, wherein the density of the biofluid is regulated to a density of between about 1.00 g/mL and about 1.15 g/mL.

13. The method of claim 1, wherein introducing the additive to alters the density of the biofluid and an aggregation potential of the non-target particles.

14. The method of claim 1, further comprising selecting the biofluid from blood buffy coat, leukapheresis product, peripheral blood, whole blood, lymph fluid, synovial fluid, spinal fluid, bone marrow, ascites fluid, and combinations or subcomponents thereof.

15. The method of claim 1, further comprising selecting the target particles to be synthetic particles selected from the group consisting of carrier particles, capture particles, enrichment particles, delivery particles, subclasses thereof, and combinations thereof.

16. The method of claim 1, further comprising selecting the target particles to be cell culture carrier particles.

17. The method of claim 1, further comprising obtaining the biofluid from a donor subject.

18. The method of claim 1, further comprising post-treating the at least one secondary stream.

19. The method of claim 18, further comprising collecting the post-treated at least one secondary stream.

20. The method of claim 18, further comprising introducing the post-treated at least one secondary stream into a recipient subject.

21. The method of claim 1, wherein the biofluid comprises the non-target particles bound to the target particles, the method further comprising treating the biofluid to unbind the non-target particles from the target particles prior to pretreating the biofluid.

22. The method of claim 1, the target particle having been introduced into the biofluid to provide a therapeutic treatment prior to pretreating the biofluid, wherein the therapeutic treatment is selected from the group consisting of delivering a therapeutic moiety, capturing a therapeutic moiety, capturing a toxin, capturing a cell type, capturing a synthetic particle, culturing a cell type, and combinations thereof.

23. The method of claim 1, further comprising flowing a second fluid adjacent to the biofluid into an inlet of the microfluidic separation channel, such that the biofluid and the second fluid flow in substantially parallel, substantially laminar flow.

24. The method of claim 1, further comprising flowing the pretreated biofluid into the inlet of the microfluidic separation channel at a flow rate of between about 0.03 mL/min to about 0.5 mL/min.

25. The method of claim 1, comprising introducing an additive to regulate the aggregation potential of the non-target particles, the non-target particles comprising erythrocytes.

26. The method of claim 1, comprising introducing an additive to regulate the aggregation potential of the non-target particles, the non-target particles comprising platelets.

27. The method of claim 1, wherein at least one of the non-target particles comprise at least one of live cells, frozen cells, preserved cells, and cells grown in a cell culture.

28. A method of separating target particles from non-target particles in a biofluid, the method comprising:
   providing the biofluid comprising the target particles and the non-target particles, the target particles being unbound;
   introducing into the biofluid an additive to regulate the density of the biofluid while preserving the integrity of the particles, wherein the density of the biofluid is regulated to substantially match a density of the target particles;

flowing the pretreated biofluid into an inlet of a microfluidic separation channel configured to maintain at least one primary stream and at least one secondary stream therewithin; and applying acoustic energy to the pretreated biofluid within the microfluidic separation channel, such that the target particles accumulate within and flow through the at least one primary stream and the non-target particles accumulate within and flow through the at least one secondary stream, the separation occurring within the microfluidic separation channel.

29. The method of claim 1, wherein the outlet includes at least one first outlet configured to receive the primary stream and a second outlet configured to receive the secondary stream.

\* \* \* \* \*